US005251614A

United States Patent [19]

Cathignol et al.

[11] Patent Number: 5,251,614

[45] Date of Patent: Oct. 12, 1993

[54] METHOD AND DEVICE INTERPOSING AN ELECTRICALLY CONDUCTIVE LIQUID BETWEEN ELECTRODES AND SHOCKWAVE APPARATUS FOR METHOD AND DEVICE

[75] Inventors: Dominique Cathignol, Genas; Jean-Louis Mestas, Chassieu; Paul Dancer, Saint Etienne; Maurice Bourlion, Saint Chamond, all of France

[73] Assignees: Technomed International, Paris; ISERM, Paris Cedex, both of France

[21] Appl. No.: 809,597

[22] Filed: Dec. 18, 1991

Related U.S. Application Data

[63] Continuation-in-part of Ser. No. 742,097, Aug. 2, 1991, Pat. No. 5,105,801, which is a continuation of Ser. No. 545,519, Jun. 28, 1990, abandoned.

[30] Foreign Application Priority Data

| | | | |
|---|---|---|---|
| Jun. 30, 1989 | [FR] | France | 89 08846 |
| Dec. 26, 1990 | [FR] | France | 90 16282 |

[51] Int. Cl.[5] .......... A61B 17/22

[52] U.S. Cl. .......... 128/24 EL

[58] Field of Search .......... 128/24 EL; 606/128

[56] References Cited

U.S. PATENT DOCUMENTS

| | | | |
|---|---|---|---|
| 2,559,227 | 7/1951 | Rieber . | |
| 3,559,435 | 2/1971 | Gerber | 72/56 |
| 4,610,249 | 9/1986 | Makofski et al. | 128/24 EL |
| 4,630,607 | 12/1986 | Duinker et al. | 128/24 EL |
| 4,651,311 | 3/1987 | Owen et al. | 367/147 |
| 4,715,375 | 12/1987 | Nowacki et al. | 128/24 EL |
| 4,715,376 | 12/1987 | Nowacki . | |
| 4,940,050 | 7/1990 | Forssmann et al. | 128/24 EL |
| 5,105,801 | 4/1992 | Cathignol et al. | 128/24 EL |

FOREIGN PATENT DOCUMENTS

| | | |
|---|---|---|
| 0296912 | 12/1988 | European Pat. Off. . |
| 1277716 | 9/1968 | Fed. Rep. of Germany . |
| 2231152 | 7/1990 | United Kingdom . |

*Primary Examiner*—Lee S. Cohen
*Assistant Examiner*—Samuel Gilbert
*Attorney, Agent, or Firm*—Cohen, Pontani, Lieberman & Pavane

[57] ABSTRACT

The present invention relates to a method and a device for producing an electric discharge between two electrodes. This method characterized in that the resistance to the passage of the electric arc, at least between the electrodes, is considerably reduced so as to bring it to a resistance value near to or slightly higher than the critical resistance, by interposing at least between the electrodes, an electrically conductive electrolyte contained in an essentially closed reservoir surrounding the electrodes. The invention makes it possible to improve the rate of discharge of an electric current produced between the electrodes, by eliminating substantially completely the latency time.

16 Claims, 3 Drawing Sheets

INVENTION

INVENTION

INVENTION

METHOD AND DEVICE INTERPOSING AN ELECTRICALLY CONDUCTIVE LIQUID BETWEEN ELECTRODES AND SHOCKWAVE APPARATUS FOR METHOD AND DEVICE

This application is a continuation in part of Ser. No. 07/742,087, now U.S. Pat. No. 5,105,801 of Aug. 2, 1991, which is a continuation application of U.S. application Ser. No. 07/545,519 of Jun. 28, 1990, abandoned.

FIELD OF THE INVENTION

The invention essentially relates to a method and device for improving in particular the reproducibility and efficiency of pressure waves generated during the electric discharge from a capacitance between two electrodes, by interposition of an electrically conductive liquid between the electrodes, and a shockwave generating apparatus using such a method or device, particularly for hydraulic lithotripsy.

BACKGROUND OF THE INVENTION

An apparatus is known from U.S. Pat. No. 2,559,227 of RIEBER, for generating high frequency shockwaves, which apparatus comprises a truncated ellipsoidal reflector in which shockwaves are generated by discharge or electric arc between two electrodes converging to the first focal point of the ellipsoid, the object being to destroy a target situated in the second focal point of the ellipsoid, which is external to the truncated reflector (see FIG. 3 and col. 7, line 51 to col. 9, line 30).

Electrodes are produced in a highly conductive material such as copper or brass and are mounted on an insulator which is supported in pivotal manner by means of a device, so as to adjust the spacing between said electrodes (see col. 4, lines 42 to 53 and col. 8, lines 40 to 47).

With the RIEBER apparatus or any similar apparatus, the discharge or electric arc is produced between the electrodes and due to the sudden discharge of a capacitor, by closing a high voltage switch (see FIG. 2B). According to the RIEBER apparatus, the circuit between the electrodes comprises a capacitor, with an associated self-inductance. It has been noted that the capacitor discharge is of damped oscillatory type. In other words, the capacitor is going to discharge and to re-charge in reverse at a lower voltage than the initial voltage which is very high, until depletion of the charges contained in the capacitor.

Simultaneously, an electric arc and a plasma are established between the two electrodes of which the current will also be, by way of consequence, of damped oscillatory type, as can be understood with reference to FIGS. 1*a*, 1*b* and 1*c*. Accordingly, FIG. 1*a* illustrates the chronogram of voltages, while FIG. 1*b* illustrates the chronogram of currents established in the RIEBER type discharge circuit. It is found that when the circuit is closed at time $t_1$, the voltage at the terminals of the electrodes rises suddenly to the value of the voltage at the terminals of the capacitors (see FIG. 1*a*). A low current is established between the two electrodes (FIG. 1*b*) due to the fact that, first the liquid in which the electrodes are immersed, and which is usually water, is still slightly electrically conductive, and second, that for reasons of safety and of arc ignition, a high resistance is provided in parallel to the capacitor supplying the electrodes.

After a certain time, namely after time $t_2$, called latency time, the arc is established between the electrodes. At that moment, the current increases suddenly by several KA as clearly illustrated in FIG. 1*b*. It is a known fact that the arc is constituted by a plasma whose resistance is extremely low (about 1/100 or 1/1000 Ohm) and it is the low value of this resistance which explains the importance of the oscillations of current (FIG. 1*b*) and of voltage (FIG. 1*a*) during the discharge of a capacitor in an RL type circuit.

The energy contained and dissipated by the arc contributes to the vaporization of the liquid in which the electrodes are immersed, and which is normally water, to the creation of a steam bubble and consequently to the formation of the shockwave. The quicker this energy is dissipated, the more efficient will be the shockwave.

It is thus found that, due to the oscillatory nature of the current, as illustrated in FIG. 1*b*, the supply of energy to the external medium is progressive, as clearly illustrated in FIG. 1*c*.

This explains how, the quicker is the vaporization of the liquid, in particular water, the stronger will be the pressure wave and the shorter will be its pressure-rising time.

Thus, a great quantity of energy will have to be delivered to vaporize an important quantity of liquid, and in particular water.

Yet, virtually all the currently known devices use discharges which are all of damped oscillatory type, as illustrated in FIGS. 1*a* and 1*b*, resulting in a progressive dissipation of the energy with time (FIG. 1*c*).

In their prior document EP-A-0 296 912, the Applicants have proposed a first solution for delivering suddenly or in a relatively short time, most of the energy stored by the charge of the capacitor of the discharge circuit between two electrodes. It was proposed to this effect, to increase the electric resistance on the path of the electric arc at least between the electrodes by interposition of a high resistance insulating element, between the arc-generating electrodes. This solution is fully satisfactory when generating shockwaves whose initial pressure wave is substantially spherical.

However, said prior solution is difficult to implement mechanically because of the small dimensions of the electrodes and of the mechanical strength towards shockwaves. Moreover, the latency time problem is not solved in that the main aim of this particular solution is only to improve the discharge rate when electric arc is established, which does not improve the reproducibility of the discharge, hence of the shockwave.

Accordingly, the main object of the invention is to solve the new technical problem consisting in providing a solution permitting instant delivery in a relatively short time of most of the energy stored by the charge of the capacitor of the discharge circuit between two electrodes, by eliminating completely or substantially the latency time normally necessary for generating an electric discharge between the electrodes.

Another object of the invention is to solve the new technical problem consisting in providing a solution permitting complete or substantially complete elimination of the latency time when generating an electric discharge between two electrodes while considerably improving the reproducibility of the shockwave due to an important improvement in localizing the generation of the discharge current.

Yet another object of the present invention is to solve the new technical problem consisting in providing a solution permitting the complete or substantially complete elimination of the latency time when generating an electric discharge between the electrodes, while producing an electric discharge of critical damped type which will cause an instant delivery or a delivery in a relatively short time of most of the energy stored by the charge of the capacitor of the discharge circuit between the electrodes.

A further object of the present invention is to solve said new technical problems while providing a solution permitting a reduction of the wear of the electrodes, and limiting the extent of the alterations to be made on the existing prior apparatuses.

Yet another object of the invention is to solve the aforesaid new technical problems in an extremely simple manner which can be used on an industrial scale, particularly with reference to extracorporeal lithotripsy.

All said new technical problems have been solved for the first time by the present invention in a satisfactory manner, for little costs, and at industrial level, particularly with reference to extracorporeal lithotripsy.

Thus, in a first aspect, the present invention provides a method for improving the electric discharge rate produced in a liquid medium such as water, between at least two electrodes, generating such a discharge, characterized in that it consists in considerably reducing the resistance to the passage of the electric discharge at least between the electrodes in order to bring it to a resistance value near to the critical resistance by interposing at least between the electrodes, an electrically conductive liquid medium contained in an essentially closed reservoir surrounding the electrodes.

Said reservoir is produced in a material which will not substantially affect the propagation of the shockwaves. Examples of such materials are a latex, a silicon, or a metal strip, which are well known to skilled in the art.

According to another advantageous embodiment, the electrodes support the reservoir and are removable. They can therefore be supplied with the reservoir, the assembly then being usable and disposable, thus reducing maintenance costs compared with the prior solutions.

According to a particularly advantageous embodiment, the electrically conductive liquid medium used has an electrical resistance which is less than 1/10, and preferably at least 1/100 of the electrical resistance value of the ordinary ionized water used as reference. Preferably still, the electrical resistance of the electrically conductive medium according to the invention, as expressed in linear resistivity, is less than about 15 Ohm.cm. The electrically conductive liquid media can be constituted by an aqueous or non-aqueous electrolyte. A suitable aqueous electrolyte is water containing ionizable compounds, notably salts such as halide salts, for example NaCl, $NH_4Cl$, sulfates or nitrates with alkaline or alkaline earth metals or transition metals such as copper. A currently preferred electrically conductive aqueous liquid medium is constituted by water salted at the rate of 100 or 200 g/l, having respectively a linear resistivity value of 10 and 5 Ohm.cm.

More preference is given to an electrically conductive aqueous liquid medium containing about 10% by weight of NaCl (about 100 g/l) and between 0.5 and 2% by weight of phosphate salt, particularly disodium phosphate ($Na_2HPO_4$, $12H_2O$). The linear resistivity of such an electrically conductive medium is about 8 Ohm.cm. Advantageously, a dye, such as methylene blue, is added in the proportion of 2 mg/l in order to reveal any leaks in the reservoir.

Suitable non-aqueous conductive liquid media include the conductive oils, rendered conductive by the addition of conductive particles such as metallic particles, which are well known to those skilled in the art.

According to a second aspect, the present invention also provides a device for improving the rate of electrical discharge produced in a liquid medium such as water, between at least two electrodes generating such a discharge, characterized in that it comprises means for reducing the resistance to the passage of an electric discharge at least between the electrodes so as to bring it to a resistance value near to the critical resistance, comprising an essentially closed reservoir surrounding the electrodes, and filled with an electrically conductive medium. The material making up said reservoir is selected not to substantially affect the propagation of the shockwaves. In particular, said reservoir can be made of latex, silicon, or metallic strip. It can take the form of a membrane around the electrodes.

According to a third aspect, the present invention further relates to an apparatus generating shockwaves by electric discharge between at least two electrodes immersed in a liquid discharge medium, notably of extracorporeal type, characterized in that it comprises a device for improving the discharge rate as described previously. According to an advantageous embodiment, said apparatus comprises a truncated ellipsoidal reflector having an internal focal point where the shockwaves are generated by electric discharge between at least two electrodes and a focus, external to the reflector, in which the shockwaves are focussed, said truncated ellipsoidal reflector being filled with a liquid coupling medium. In this case, there is an essentially closed reservoir, as indicated hereinabove, which surrounds the electrodes and therefore the internal focus, which reservoir is filled with electrically conductive medium, while outside said reservoir, another liquid medium, notably water, is used inside the truncated ellipsoidal reflector.

Other characteristics of the electrically conductive medium according to the invention have been described with reference to the method and are obviously applicable to the device.

According to the invention, the discharge is produced through an electrically conductive medium, thus eliminating completely or substantially completely the latency time. Moreover, a considerable increase of the reproducibility of the shockwave generated between the electrodes is obtained. This is mainly due to the fact that in the conventional case, the arc is ignited at random in time and in space, inducing the formation of an inaccurately localized steam bubble, which is not the case according to the present invention. Also, according to the invention, the presence of an oscillating current is eliminated, so that the discharge is of critical damped type, as will be more readily understood from the description given with reference to the appended drawing.

Also according to the invention, the presence of the reservoir filled with electrically conductive liquid, enables the quantity of electrically conductive liquid used to be considerably reduced, and this liquid is not in contact with the patient. Moreover, the electric discharge takes place in a confined domain, thereby limiting electrical risks.

The invention therefore provides all the technical advantages indicated hereinabove, which were unexpected and non-obvious to the man skilled in the art.

Other aims, characteristics and advantages of the invention will also appear to the man skilled in the art from the following explanatory description made with reference to the accompanying drawings, particularly showing a presently preferred embodiment of the invention, given by way of example and non-restrictively

DETAILED DESCRIPTION OF PREFERRED EMBODIMENTS

Figure 2:
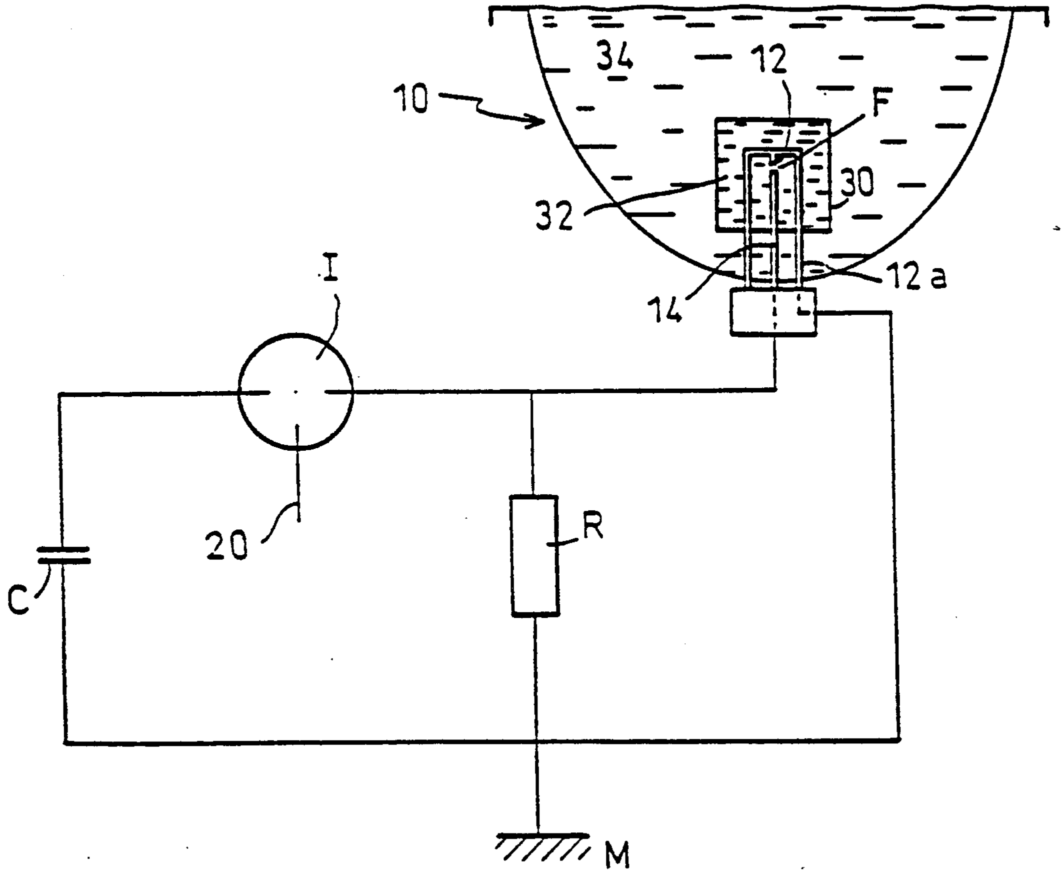
FIG. 2 illustrates diagrammatically, in partial cross-section, an apparatus generating shockwaves, particularly for extracorporeal lithotripsy, comprising an electric discharge device according to the present invention, which comprises a substantially closed reservoir filled with an electrically conductive liquid medium in which the electrical discharge is generated between two electrodes.

With reference to FIG. 2, this shows an apparatus generating shockwaves such as for extracorporeal lithotripsy, comprising a truncated ellipsoidal reflector designated by the general reference 10 which is of the type of that described in U.S. Pat. No. 2,559,227 of RIEBER. Said reflector is provided with two discharge electrodes 12, 14 disposed in facing relationship, in this case, according to a cage-like structure as is known from document DE-A-2 635 635. These two discharge electrodes 12, 14 converge towards the internal focus point symbolized by reference F.

The second focal point of the ellipsoid is situated outside the truncated ellipsoidal reflector 10 and it is with that second focus point that the target to be destroyed will be made to coincide, as described in detail in RIEBER's U.S. patent. Said target, of course, can be constituted by a concretion. The electrode 12 is for example on ground as illustrated in the figure, and connected also to one side of a capacitor C. The other electrode 14 is connected to the capacitor C via a switching device I, such as for example a gas discharge arrester or "spark gap", which is intermittently switched off by a control symbolically designated by reference 20. A high value resistor R or a self is provided in parallel to capacitor C. The capacitor is charged with a high voltage, between 10,000 and 20,000 V, from a source of power as described for example in FIG. 1 of Applicants' document EP-A-0 296 912, this circuit not being illustrated here.

According to the prior art, the ellipsoidal reflector 10 is filled with a shockwave transmitting liquid, usually water, whose resistance to the passage of an electrical current is significant. Said electrical resistance value of ordinary ionized water such as tap water, as expressed in linear resistivity value, is, in average, about 1500 Ohm.cm. In the case of oils, which are very insulating, such as in the case of RIEBER's U.S. Pat. No. 2,559,227, the linear resistivity value is about 3 to 5M. Ohm.cm.

Figure 1A:
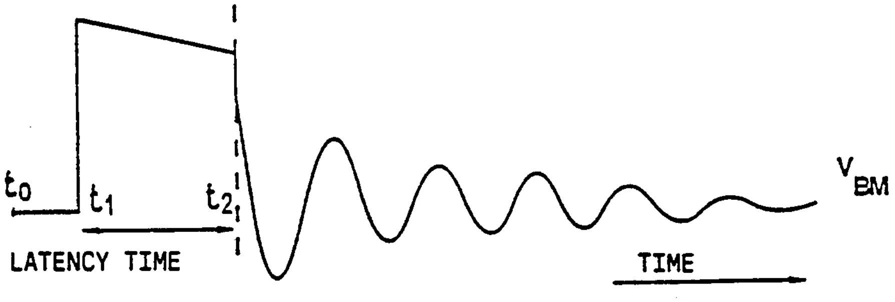
FIG. 1a PRIOR ART
FIGS. 1*a*, 1*b* and 1*c* respectively show the curves of voltage, current and energy during the conventional discharge of an electric arc generated between two electrodes using a discharge circuit according to U.S. Pat. No. 2,559,227 of RIEBER.
Figure 1B:
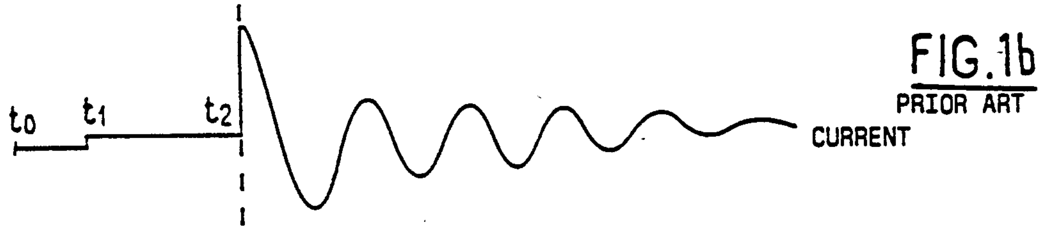
FIG. 1b PRIOR ART
Figure 1C:
FIG. 1c PRIOR ART

When producing an electric discharge in such a prior art circuit, where the liquid medium between the electrodes 12, 14 is constituted by normally ionized water, a discharge chronogram such as illustrated in FIGS. 1*a*, 1*b* and 1*c*, is obtained for which there is a significant latency time while the discharge rate is of the oscillatory type, this delivering the energy progressively to the external medium.

According to the present invention, an essentially closed reservoir 30 is used, which is filled with an electrically conductive medium 32, thus enabling the resistance to the passage of the electric discharge between the electrodes 12, 14 to be brought near to or advantageously below the critical resistance this constituting a solution which is quite the opposite to that recommended in Applicants' document EP-A-0 296 912 which proposes on the contrary to considerably increase the electrical resistance between the electrodes by interposing an insulating element between the electrodes.

This reservoir 30 is itself surrounded by a liquid coupling medium 34 filling the truncated ellipsoidal reflector 10, particularly water, this enabling the patient's skin to be in contact with ordinary water.

This reservoir is produced in a material which does not substantially affect the shockwaves generated by the electric discharge between the electrodes 12, 14. Such materials are wellknown of the man skilled in the art. Particular examples of such materials are a latex, a silicon, a metallic strip. Practical embodiments take the form of a membrane fixed in appropriate manner, for example on the electrically conductive external element 12*a* supporting the electrode, as understood by the man skilled in the art.

Advantageously, the electrodes are designed to support the reservoir, and are removable, as illustrated in FIG. 2. They can therefore be supplied with the reservior 30, the electrodes and reservoir assembly being then usable and disposable, thereby reducing maintenance costs compared with the prior solutions.

According to an advantageous embodiment of the invention, the electrically conductive liquid medium 32, contained in the reservoir 30, has an electrical resistance which is less than 1/10 and preferably less than 1/100 of the value of the electrical resistance of ordinary ionized water, used as reference, and which is usually of about 1500 Ohm.cm as expressed in linear resistivity. Preferably, the electrical resistance of the electrically conductive medium according to the invention, as expressed in linear resistivity, is less than about 15 Ohm.cm.

Any aqueous or non-aqueous electrically conductive liquid can be used as electrically conducting medium according to the invention. A suitable aqueous electrically conductive liquid is an aqueous electrolyte constituted from pure water to which ionizable soluble compounds are added, such as salts like halides, in particular chlorides, sulfates, nitrates. A particularly preferred aqueous electrolyte is water with addition of NaCl or of $NH_4Cl$. The medium given more preference is water salted at 100 or 200 g/l whose respective linear resistivity is from 10 to 5 Ohm.cm.

More preference is given to an aqueous electrically conductive medium which contains about 10% by weight of NaCl and between 0.5 and 2% by weight of disodium phosphate ($Na_2HPO_4,12H_2O$) and which has a linear resistivity of about 8 Ohm.cm at 25° . The NaCl/phosphate proportion is not critical and enables the resistivity to be adjusted to up to 10 Ohm.cm. A dye can also be added to the electrically conductive medium, so as to reveal any leaks in the reservoir 30.

Suitable non-aqueous electrolytes are electrically conductive oils, namely oils which have been made conductive by addition of electrically conductive particles such as metallic particles.

Figure 3A:
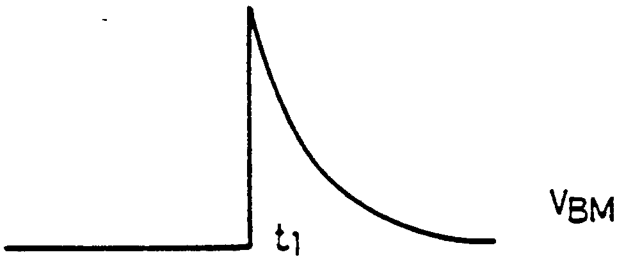
FIGS. 3*a*3*b*, 3*c* respectively illustrate, similarly to FIGS. 1*a*, 1*b*, 1*c* the curves of voltage, current and energy obtained according to the present invention, using an electrically conductive liquid medium interposed at least between the electrodes, according to FIG. 2.
Figure 3B:
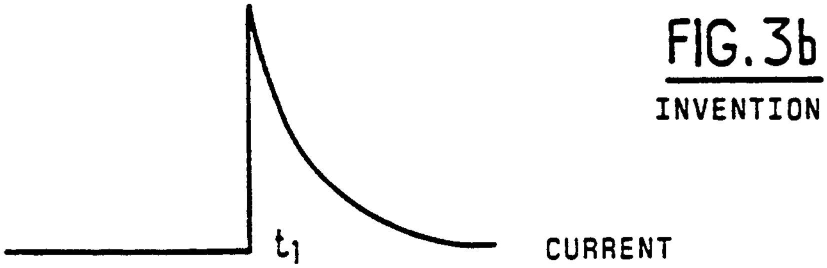
Figure 3C:
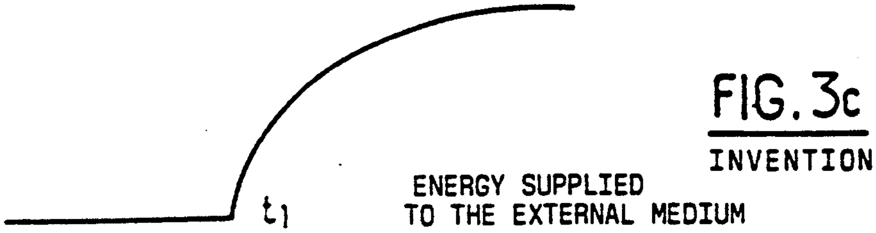

According to the invention, when using an electrically conductive medium, a discharge chronogram is obtained, such as illustrated in FIGS. 3a, 3b, 3c. It is found that, as soon as the electrodes are charged at time $t_1$, the generation of the arc is quasi-instantaneous. Moreover, said discharge is of critical damped type, and is no longer of the oscillatory type. Also, the energy is delivered to the external medium for a much shorter time than in the case of an oscillating rate, or in the case of prior rates with latency times.

The result is a considerable increase of the reproducibility of the pressure wave owing to the fact that the discharge is no longer ignited at random in time and in space, but on the contrary at time $t_1$ and induces the formation of a perfectly localized steam bubble. The chronogram shown in FIG. 3 was obtained by using water salted at 200 g/l as electrically conducting medium for immersing the electrodes 12, 14, as well as a capacitor having a capacitance of 100 nF, a spacing between the electrodes of 0.4 mm, the discharge circuit of FIG. 2 having a total self inductance L of 80 nH.

In the description and claims, it will be recalled that the critical resistance is the value of the resistance between the electrodes for which the relation:

$$R_c = \sqrt{\frac{L}{C}}$$

is substantianlly met. In the formula L is the value of internal self-inductance of the dischage circuit of capacitor C, and C is the capacitance value of the capacitor.

It will be noted that according to the invention, using an electrically conductive liquid medium, an excellent reproducibility of the shockwaves is obtained, the dispersion coefficient being less than 5%, particularly if salted water is used, whereas said mean deviation is about 30% if ordinary ionized water such as tap water is used. The invention therefore provides all the aforesaid non-obvious and unexpected technical advantages and as a result solves all the aforesaid technical problems. The invention also provides the possibility of implementing the aforedescribed method.

Finally, the invention also covers an apparatus generating shockwaves by generating an electric arc between two electrodes, characterized in that it uses a method or device for improving the discharge rate such as described hereinabove. In particular, said apparatus for generating shockwaves is characterized in that it comprises a truncated ellipsoidal reflector comprising a reservoir filled with an electrically conductive liquid, as previously described, as well as another liquid coupling medium surrounding the reservoir and filling the reflector. A particular application is extracorporeal lithotripsy.

What is claimed is:

1. A method for improving reproducibility of electric discharge produced in a liquid medium confined in a housing for producing shockwaves, comprising the steps of:

providing in said housing filled with a liquid medium two closely-spaced discharge electrodes forming part of a discharge circuit having an inductance L and a capacitance C defining a critical resistance $R_c$ equal to $\sqrt{L/C}$;

disposing an enclosure about said electrodes in said housing;

filling said enclosure with an electrically conductive liquid medium having an electrical resistance providing said discharge circuit with an electrical resistance value at or near the critical resistance $R_c$; and intermittently feeding said electrodes with electric current for producing a discharge therebetween.

2. The method of claim 1, wherein the electrical resistance of said electrically conductive liquid medium is less than 1/10 of the electrical resistance of ordinary ionized water.

3. The method of claim 1, wherein the electrical resistance of said electrically conductive liquid medium, as expressed in linear resistivity, is less than about 15 Ohm.cm.

4. The method of claim 1, wherein the electrically conductive liquid medium comprises at least one of an aqueous or non-aqueous electrolyte.

5. The method of claim 4, wherein said electrically conductive liquid medium comprises salted water.

6. A device for improving reproducibility of an electrical discharge for producing shockwaves, comprising:

a housing containing a liquid medium;

a pair of closely-spaced discharge electrodes disposed in said housing and forming part of a discharge circuit having an inductance L and a capacitance C defining a critical resistance Rc equal to $\sqrt{L/C}$;

an enclosure disposed about said electrodes in said housing;

an electrically conductive liquid medium filling said enclosure, said electrically conductive liquid medium having an electrical resistance providing said discharge circuit with an electrical resistance value at or near the critical resistance; and means for intermittently feeding said electrodes with electric current for producing a discharge therebetween.

7. The device of claim 6, wherein the electrodes support the enclosure, and wherein said electrodes with said supported enclosure are removably secured to said housing.

8. The device of claim 6, wherein said electrically conductive liquid medium has an electrical resistance, expressed in terms of linear resistivity, which is less than 1/10 of the electrical resistance of ordinary ionized water.

9. The device of claim 8, wherein the electrically conductive liquid medium comprises at least one of an aqueous or non-aqueous electrolyte.

10. The device of claim 8, wherein the electrically conductive liquid medium is an aqueous electrolyte comprising pure water and at least one added ionizable compound.

11. The device of claim 8, wherein the electrically conductive liquid medium has an electrical resistance, expressed in terms of linear resistivity, less than about 15 Ohm.cm.

12. The device of claim 8, wherein the electrically conductive liquid medium is an aqueous electrolyte comprising pure water, 10% by weight of sodium chloride and 0.5 to 2% by weight of sulfate.

13. The apparatus of claim 6 wherein said housing comprises a truncated ellipsoidal reflector.

14. The device of claim 10, wherein said at least one added ionizable compound comprises at least one of a halide salt, a sulfate or a nitrate.

15. The device of claim 12, wherein said sulfate comprises disodium sulfate.

16. A method for improving reproducibility of electric discharge produced in a liquid medium confined in a housing for producing shockwaves for practicing extracorporeal lithotripsy, comprising the steps of:

providing in said housing filled with a liquid medium two closely-spaced discharge electrodes forming part of a discharge circuit having an inductance L and a capacitance C defining a critical resistance $R_c$ equal to $\sqrt{L/C}$;

disposing an enclosure about said electrodes in said housing;

filling said enclosure with an electrically conductive liquid medium having an electrical resistance providing said discharge circuit with an electrical resistance value at or near the critical resistance $R_c$;

disposing said housing adjacent a subject for practicing extracorporeal lithotripsy; and intermittently feeding said electrodes with an electric current for producing a discharge therebetween.

* * * * *